(12) United States Patent
Brown et al.

(10) Patent No.: US 7,814,143 B2
(45) Date of Patent: Oct. 12, 2010

(54) SYSTEM AND METHOD FOR MODIFYING DOCUMENTS SENT OVER A COMMUNICATIONS NETWORK

(75) Inventors: Stephen James Brown, Woodside, CA (US); Konstantin Othmer, Mountain View, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 1093 days.

(21) Appl. No.: 11/301,331

(22) Filed: Dec. 13, 2005

(65) Prior Publication Data

US 2006/0089969 A1   Apr. 27, 2006

Related U.S. Application Data

(63) Continuation of application No. 09/540,482, filed on Mar. 31, 2000, now abandoned, which is a continuation of application No. 09/394,219, filed on Sep. 13, 1999, now Pat. No. 6,375,469, which is a continuation of application No. 08/814,293, filed on Mar. 10, 1997, now Pat. No. 5,951,300.

(51) Int. Cl.
 *G06F 15/16* (2006.01)
(52) U.S. Cl. ............... 709/203; 709/223; 705/2; 715/234; 600/301
(58) Field of Classification Search ................. 709/203, 709/223
See application file for complete search history.

(56) References Cited

U.S. PATENT DOCUMENTS

| | | | |
|---|---|---|---|
| 3,426,150 A | 2/1969 | Tygart | |
| 3,566,365 A | 2/1971 | Rawson et al. | |
| 3,566,370 A | 2/1971 | Worthington, Jr. et al. | |
| 3,581,072 A | 5/1971 | Nymeyer | |
| 3,768,014 A | 10/1973 | Smith | |
| 3,811,116 A | 5/1974 | Takeuchi et al. | |
| 3,883,235 A | 5/1975 | Lynn et al. | |

(Continued)

FOREIGN PATENT DOCUMENTS

EP    0286456    10/1988

(Continued)

OTHER PUBLICATIONS

+5V Powered Isolated RS-232 Drivers/Receivers Maxim Integrated Products.

(Continued)

*Primary Examiner*—Tammy T Nguyen
(74) *Attorney, Agent, or Firm*—Christopher P. Maiorana, PC

(57) ABSTRACT

A system and method applied to a communications network which transmits document portions in which an original document portion having an identifier portion and an information portion is replaced or swapped with a substitute null document portion. The reads the identifier portion of the original document portion, determines the information portion of the original document portion, and issue a swap order when an undesired original document portion is found. A modified document is created by inserting the substitute null document portion in place of the undesired portion and the modified document is passed on to the user set and displayed. Also, the system performs detection and replacement of undesired content in emails, such as junk mail, viruses and confidential material.

20 Claims, 6 Drawing Sheets

U.S. PATENT DOCUMENTS

| | | |
|---|---|---|
| 3,910,257 A | 10/1975 | Fletcher et al. |
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia |
| 4,674,652 A | 6/1987 | Aten et al. |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A | 2/1989 | Fu et al. |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,916,441 A | 4/1990 | Gombrich |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,552 A | 7/1992 | Fang et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |

| | | | | | |
|---|---|---|---|---|---|
| 5,333,981 A | 8/1994 | Pronovost et al. | 5,635,532 A | 6/1997 | Samid |
| 5,335,338 A | 8/1994 | Proesel | 5,640,569 A | 6/1997 | Miller et al. |
| 5,339,821 A | 8/1994 | Fujimoto | 5,640,953 A | 6/1997 | Bishop et al. |
| 5,341,291 A | 8/1994 | Roizen et al. | 5,642,731 A | 7/1997 | Kehr |
| 5,343,239 A | 8/1994 | Lappington et al. | 5,642,936 A | 7/1997 | Evans |
| 5,344,324 A | 9/1994 | O'Donnell et al. | 5,651,363 A | 7/1997 | Kaufman et al. |
| 5,357,427 A | 10/1994 | Langen et al. | 5,651,775 A | 7/1997 | Walker et al. |
| 5,366,896 A | 11/1994 | Margrey et al. | 5,659,691 A | 8/1997 | Durward et al. |
| 5,368,562 A | 11/1994 | Blomquist et al. | 5,666,487 A | 9/1997 | Goodman et al. |
| 5,371,687 A | 12/1994 | Holmes, II et al. | 5,670,711 A | 9/1997 | Detournay et al. |
| 5,375,604 A | 12/1994 | Kelly et al. | 5,675,635 A | 10/1997 | Vos et al. |
| 5,377,100 A | 12/1994 | Pope et al. | 5,678,562 A | 10/1997 | Sellers |
| 5,390,238 A | 2/1995 | Kirk et al. | 5,678,571 A | 10/1997 | Brown |
| 5,399,821 A | 3/1995 | Inagaki et al. | 5,679,075 A | 10/1997 | Forrest et al. |
| 5,410,471 A | 4/1995 | Alyfuku et al. | 5,680,590 A | 10/1997 | Parti |
| 5,410,474 A | 4/1995 | Fox | 5,680,866 A | 10/1997 | Kangas et al. |
| 5,429,140 A | 7/1995 | Burdea et al. | 5,687,322 A | 11/1997 | Deaton et al. |
| 5,431,690 A | 7/1995 | Schaldach et al. | 5,687,717 A | 11/1997 | Halpern et al. |
| 5,431,691 A | 7/1995 | Snell et al. | 5,687,734 A | 11/1997 | Dempsey et al. |
| 5,434,611 A | 7/1995 | Tamura | 5,689,652 A | 11/1997 | Lupien et al. |
| 5,438,607 A | 8/1995 | Przygoda, Jr. et al. | 5,692,906 A | 12/1997 | Corder |
| 5,438,983 A | 8/1995 | Falcon | 5,704,364 A | 1/1998 | Saltzstein et al. |
| 5,441,047 A | 8/1995 | David et al. | 5,704,366 A | 1/1998 | Tacklind et al. |
| 5,449,334 A | 9/1995 | Kingsbury | 5,704,902 A | 1/1998 | Vandenbelt et al. |
| 5,454,721 A | 10/1995 | Kuch | 5,704,922 A | 1/1998 | Brown |
| 5,454,722 A | 10/1995 | Holland et al. | 5,710,178 A | 1/1998 | Samid |
| 5,456,606 A | 10/1995 | McIntyre | 5,710,918 A | 1/1998 | Lagarde et al. |
| 5,456,692 A | 10/1995 | Smith, Jr. et al. | 5,711,297 A | 1/1998 | Iliff |
| 5,458,123 A | 10/1995 | Unger | 5,714,319 A | 2/1998 | Joutel et al. |
| 5,467,269 A | 11/1995 | Flaten | 5,715,451 A | 2/1998 | Marlin |
| 5,471,039 A | 11/1995 | Irwin, Jr. et al. | 5,715,823 A | 2/1998 | Wood et al. |
| 5,471,382 A | 11/1995 | Tallman et al. | 5,717,739 A | 2/1998 | Dyer et al. |
| 5,483,276 A | 1/1996 | Brooks et al. | 5,717,913 A | 2/1998 | Driscoll |
| 5,488,412 A | 1/1996 | Majeti et al. | 5,720,733 A | 2/1998 | Brown |
| 5,488,423 A | 1/1996 | Walkingshaw et al. | 5,722,418 A | 3/1998 | Bro |
| 5,501,231 A | 3/1996 | Kaish | 5,727,153 A | 3/1998 | Powell |
| 5,502,636 A | 3/1996 | Clarke | 5,730,124 A | 3/1998 | Yamauchi |
| 5,502,726 A | 3/1996 | Fischer | 5,730,654 A | 3/1998 | Brown |
| 5,504,519 A | 4/1996 | Remillard | 5,732,696 A | 3/1998 | Rapoport et al. |
| 5,517,405 A | 5/1996 | McAndrew et al. | 5,732,709 A | 3/1998 | Tacklind et al. |
| 5,518,001 A | 5/1996 | Snell | 5,734,413 A | 3/1998 | Lappington et al. |
| 5,519,058 A | 5/1996 | Gonick et al. | 5,749,083 A | 5/1998 | Koda et al. |
| 5,519,433 A | 5/1996 | Lappington et al. | 5,752,234 A | 5/1998 | Withers |
| 5,523,232 A | 6/1996 | Sechler | 5,754,740 A | 5/1998 | Fukuoka et al. |
| 5,536,249 A | 7/1996 | Castellano et al. | 5,760,771 A | 6/1998 | Blonder et al. |
| 5,542,420 A * | 8/1996 | Goldman et al. ............ 600/301 | 5,772,585 A | 6/1998 | Lavin et al. |
| 5,544,649 A | 8/1996 | David et al. | 5,778,882 A | 7/1998 | Raymond et al. |
| 5,546,943 A | 8/1996 | Gould | 5,782,814 A | 7/1998 | Brown et al. |
| 5,549,117 A | 8/1996 | Tacklind et al. | 5,785,650 A | 7/1998 | Akasaka et al. |
| 5,550,575 A | 8/1996 | West et al. | 5,787,295 A | 7/1998 | Nakao |
| 5,553,609 A | 9/1996 | Chen et al. | 5,791,342 A | 8/1998 | Woodard |
| 5,558,638 A | 9/1996 | Evers et al. | 5,792,117 A | 8/1998 | Brown |
| 5,564,429 A | 10/1996 | Bornn et al. | 5,793,969 A | 8/1998 | Kamentsky et al. |
| 5,569,212 A | 10/1996 | Brown | 5,794,219 A | 8/1998 | Brown |
| 5,572,421 A | 11/1996 | Altman et al. | 5,794,251 A | 8/1998 | Watanabe et al. |
| 5,572,646 A | 11/1996 | Kawai et al. | 5,796,393 A | 8/1998 | MacNaughton |
| 5,574,828 A | 11/1996 | Hayward et al. | 5,799,318 A | 8/1998 | Cardinal et al. |
| 5,576,952 A | 11/1996 | Stutman et al. | 5,800,458 A | 9/1998 | Wingrove |
| 5,583,758 A | 12/1996 | McIlroy et al. | 5,802,494 A | 9/1998 | Kuno |
| 5,590,648 A | 1/1997 | Mitchell et al. | 5,802,534 A | 9/1998 | Hatayama et al. |
| 5,593,349 A | 1/1997 | Miguel et al. | 5,806,057 A | 9/1998 | Gormley et al. |
| 5,593,390 A | 1/1997 | Castellano et al. | 5,810,747 A | 9/1998 | Brudny et al. |
| 5,594,637 A | 1/1997 | Eisenberg et al. | 5,819,735 A | 10/1998 | Mansfield et al. |
| 5,596,994 A | 1/1997 | Bro | 5,822,544 A | 10/1998 | Chaco et al. |
| 5,597,307 A | 1/1997 | Redford et al. | 5,822,715 A | 10/1998 | Worthington et al. |
| 5,601,435 A | 2/1997 | Quy | 5,825,283 A | 10/1998 | Camhi |
| 5,613,495 A | 3/1997 | Mills et al. | 5,827,180 A | 10/1998 | Goodman |
| 5,619,991 A | 4/1997 | Sloane | 5,828,943 A | 10/1998 | Brown |
| 5,624,265 A | 4/1997 | Redford et al. | 5,832,448 A | 11/1998 | Brown |
| 5,628,309 A | 5/1997 | Brown | 5,835,896 A | 11/1998 | Fisher et al. |
| 5,629,981 A | 5/1997 | Nerlikar | 5,840,020 A | 11/1998 | Heinonen et al. |
| 5,631,844 A | 5/1997 | Margrey et al. | 5,842,976 A | 12/1998 | Williamson |
| 5,633,910 A | 5/1997 | Cohen | 5,867,821 A * | 2/1999 | Ballantyne et al. ............. 705/2 |

| | | | | | | |
|---|---|---|---|---|---|---|
| 5,868,669 A | 2/1999 | Iliff | | 6,270,456 B1 | 8/2001 | Iliff |
| 5,868,683 A | 2/1999 | Protopapas et al. | | 6,334,778 B1 | 1/2002 | Brown |
| 5,875,432 A | 2/1999 | Sehr | | 6,352,523 B1 | 3/2002 | Brown et al. |
| 5,879,163 A | 3/1999 | Brown et al. | | 6,368,273 B1 | 4/2002 | Brown |
| 5,882,338 A | 3/1999 | Gray | | 6,370,513 B1 | 4/2002 | Kolawa et al. |
| 5,887,133 A | 3/1999 | Brown et al. | | 6,375,469 B1 | 4/2002 | Brown |
| 5,893,077 A | 4/1999 | Griffin | | 6,379,301 B1 | 4/2002 | Worthington et al. |
| 5,893,098 A | 4/1999 | Peters et al. | | 6,381,577 B1 | 4/2002 | Brown |
| 5,897,493 A | 4/1999 | Brown | | 6,436,036 B1 | 8/2002 | Miller-Kovach et al. |
| 5,899,855 A | 5/1999 | Brown | | 6,513,532 B2 | 2/2003 | Mault et al. |
| 5,911,687 A | 6/1999 | Sato et al. | | 2002/0019748 A1 | 2/2002 | Brown |
| 5,913,310 A | 6/1999 | Brown | | 2004/0106855 A1 | 6/2004 | Brown |
| 5,918,603 A | 7/1999 | Brown | | 2004/0107116 A1 | 6/2004 | Brown |
| 5,920,477 A | 7/1999 | Hofbert et al. | | 2004/0117207 A1 | 6/2004 | Brown |
| 5,926,526 A * | 7/1999 | Rapaport et al. ......... 379/88.25 | | 2004/0117208 A1 | 6/2004 | Brown |
| 5,933,136 A | 8/1999 | Brown | | 2004/0117209 A1 | 6/2004 | Brown |
| 5,935,060 A | 8/1999 | Iliff | | 2004/0117210 A1 | 6/2004 | Brown |
| 5,940,801 A | 8/1999 | Brown | | | | |
| 5,941,829 A | 8/1999 | Saltzstein et al. | | FOREIGN PATENT DOCUMENTS | | |
| 5,945,651 A | 8/1999 | Chorosinski et al. | | | | |
| 5,951,300 A | 9/1999 | Brown | | EP | 0320749 | 6/1989 |
| 5,954,641 A | 9/1999 | Kehr et al. | | EP | 370599 | 5/1990 |
| 5,956,501 A | 9/1999 | Brown | | EP | 0461910 | 12/1991 |
| 5,960,403 A | 9/1999 | Brown | | EP | 508912 | 10/1992 |
| 5,961,446 A | 10/1999 | Beller et al. | | EP | 526166 | 2/1993 |
| 5,966,526 A | 10/1999 | Yokoi | | EP | 0558975 | 9/1993 |
| 5,971,855 A | 10/1999 | Ng | | EP | 0653718 | 5/1995 |
| 5,971,922 A | 10/1999 | Arita et al. | | EP | 676709 | 10/1995 |
| 5,983,003 A | 11/1999 | Lection et al. | | EP | 680727 | 11/1995 |
| 5,983,217 A | 11/1999 | Khosravi-Sichani et al. | | EP | 761160 | 3/1997 |
| 5,987,471 A | 11/1999 | Bodine et al. | | EP | 08131551 | 12/1997 |
| 5,995,969 A | 11/1999 | Lee et al. | | EP | 0251520 | 1/1998 |
| 5,997,476 A | 12/1999 | Brown | | GB | 2218831 | 11/1989 |
| 5,997,502 A | 12/1999 | Reilly et al. | | GB | 2225637 | 6/1990 |
| 6,001,065 A | 12/1999 | DeVito | | JP | 54005785 | 1/1979 |
| 6,022,315 A | 2/2000 | Iliff | | JP | 54146633 | 11/1979 |
| 6,022,615 A | 2/2000 | Rettenbacher | | JP | 62226278 | 10/1987 |
| 6,023,686 A | 2/2000 | Brown | | JP | 5155024 | 6/1993 |
| 6,024,281 A | 2/2000 | Shepley | | JP | 5266002 | 10/1993 |
| 6,029,138 A | 2/2000 | Khorasani et al. | | JP | 199540709596 | 4/1995 |
| 6,032,119 A | 2/2000 | Brown et al. | | WO | WO-8501667 | 4/1985 |
| 6,035,328 A | 3/2000 | Soukal | | WO | WO-90/00367 | 1/1990 |
| 6,046,761 A | 4/2000 | Echerer | | WO | WO-9109374 | 6/1991 |
| 6,049,794 A | 4/2000 | Jacobs et al. | | WO | WO-93/01489 | 1/1993 |
| 6,050,940 A | 4/2000 | Braun et al. | | WO | WO-9302622 | 2/1993 |
| 6,055,314 A | 4/2000 | Spies et al. | | WO | WO-9416774 | 8/1994 |
| 6,055,487 A | 4/2000 | Margery et al. | | WO | WO-95/09386 | 4/1995 |
| 6,055,506 A | 4/2000 | Frasca, Jr. | | WO | WO-95/20199 | 7/1995 |
| 6,057,758 A | 5/2000 | Dempsey et al. | | WO | WO-9522131 | 8/1995 |
| 6,068,615 A | 5/2000 | Brown et al. | | WO | WO-9529447 | 11/1995 |
| 6,095,985 A | 8/2000 | Raymond et al. | | WO | WO-96/07908 | 3/1996 |
| 6,101,478 A | 8/2000 | Brown | | WO | WO-96/25877 | 8/1996 |
| 6,101,510 A * | 8/2000 | Stone et al. ................ 715/234 | | WO | WO-9636923 | 11/1996 |
| 6,110,148 A | 8/2000 | Brown et al. | | WO | WO-97/08605 | 3/1997 |
| 6,113,578 A | 9/2000 | Brown | | WO | WO-97/12544 | 4/1997 |
| 6,138,145 A | 10/2000 | Kawanaka | | WO | WO-9737738 | 10/1997 |
| 6,144,837 A | 11/2000 | Quy | | WO | WO-98/16895 | 4/1998 |
| 6,151,586 A | 11/2000 | Brown | | WO | WO-9831275 | 7/1998 |
| 6,161,095 A | 12/2000 | Brown | | WO | WO-9839933 | 9/1998 |
| 6,167,362 A | 12/2000 | Brown et al. | | | | |
| 6,167,386 A | 12/2000 | Brown | | | | |
| 6,168,563 B1 | 1/2001 | Brown | | | | |
| 6,177,940 B1 | 1/2001 | Bond et al. | | | | |
| 6,186,145 B1 | 2/2001 | Brown | | | | |
| 6,189,029 B1 | 2/2001 | Fuerst | | | | |
| D439,242 S | 3/2001 | Brown et al. | | | | |
| 6,210,272 B1 | 4/2001 | Brown | | | | |
| 6,221,012 B1 | 4/2001 | Maschke et al. | | | | |
| 6,233,539 B1 | 5/2001 | Brown | | | | |
| 6,240,393 B1 | 5/2001 | Brown | | | | |
| 6,248,065 B1 | 6/2001 | Brown | | | | |
| 6,260,022 B1 | 7/2001 | Brown | | | | |
| 6,270,455 B1 | 8/2001 | Brown | | | | |

OTHER PUBLICATIONS

Adilman; "Videogames: Knowing the Score"; Creative Computing; v9; p. 224(5); Dec. 1983; Dialog: File 148, Acc# 01891055.

AdOptimizer—Ad Management Software For Websites, Newsbytes, pNEW10040041, Oct. 4, 1996.

Albisser, A.M. "Intelligent Instrumentation in Diabetic Management", CRC Critical Reviews in Biomedical Engineering, vol. 17, No. 1, pp. 1-24.

Anonymous, "Health Hero Network, Inc. Receives First-Ever FDA Clearance for Connecting Medical Devices to Internet", PR Newswire, (Dec. 2, 1993), 3 pages.

Antique Collector , Putting the Lot on the Net, vol. 66, Issue 9, p. 26, Downloaded from Corporate Resource Net, Nov./Dec. 1995.

Bai, "Design of home healthcare network", IEEE 1997 pp. 1657-1658.

Billiard, A., et al. "Telematic Transmission of Computerized Blood Glucose Profiles for IDDm Patients", Diabetes Care, (Feb. 1991), vol. 14, No. 2, pp. 130-134.

Blood Glucose Monitors, Portable Health Device, (1998), vol. 17(9), pp. 253-271.

Bower, "Brain Clues to Energy-efficient Learning", Science News, (Apr. 1992), v. 141; p215(1); Dialog: File 647, Acct# 12123949.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bruce, "Health Hero Network CEO, CNNfn", Digital Jam, (Dec. 1, 1999), 3.

Bruce, et al., "The Effects of Sympathetic Nervous System Activation and Psychological Stress . . . "; Diabetologia; 35(9); 1992; 835-843; Dialog: File 5, Acc#9629427. (9 pages).

Brunetti, P., et al., "A Simulation Study on a Self-Turning Portable Controller of Blood Glucose", The International Journal of Artificial Organs, (1993), vol. 16, No. 16, pp. 51-57.

Caprihan, A., et al., "A Simple Microcomputer for Biomedical Signal Processing", IECI '78 Annual Conference Proceedings on Industrial Applications of Microprocessors, (Mar. 20, 1978), 18-23.

Cathay Pacific Airways-USA receives more than 1,300 bids during first five days of CyberAuction; Business Wire, Oct. 18, 1995, p10181119.

Cathay Pacific Airways-USA to Hold First-Ever Internet CyberAuction; CyberTravelers Can Bid for 50 Business Class Round Trips to Hong Kong—No Minimum Bid; Business Wire; p9261084; Sep. 26, 1995; Dialog: File 148, Acc#08167091.

CD-ROM Mavericks: Proprietary TV-Based Players, Byte Guide to CD-ROM, pp. 100-105.

Central Fetal Monitoring Systems with Optical Disk Storage, New Technology Brief, (Nov./Dec. 1998), vol. 2, No. 6, pp. 249-251.

Cheng, Joe H., "PCT Search Report", (Jan. 11, 1996).

DigiPet Instruction Manual, 1997.

Digital Doggie; retrieved from URL http://www.virtualpet.com/vp/farm/gigapet/ddoggie.htm Apr. 23, 2000.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Edelson; "Fashion Reevaluates Flickering Fortunes of TV Home Shopping"; WWD; v170 n87; p1(3); Nov. 8, 1995; Dialog: File 148, Acc#08289119.

EP European Search Report, From 6858P005EP, (Mar. 27, 1998).

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Finston, "Parent + Teacher = Healthy Child", Diabetes Forecast, (Apr. 1994), v47 n9; P26(5); Dialog: file 149, Acc# 15804228.

Fox, "Not My Type: Type B Behavior, Type I Diabetes Plus Stress Equals Blood Sugar Blues", Health, (Mar. 1998), v20 n3; pp. 22(1); Dialog: File 149, Acc# 06397959.

Franklin; "Proposed Auction Rules for PCS: The FCC Plans to Use Competitive Bidding, but Exact Procedures are Undefined"; Cellular Business; v10 n13; p. 18(2); Dec. 1993; Dialog: File 148, Acc#06787310.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Future of the Virtual Pet Industry, 1997 [retrieved on Apr. 23, 2000], Retrieved from <URL:www.virtualpet.com/vp/ future/future.htm>.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Gauntlet (for PC) rulebook by Mindscape Inc. (Gauntlet by Apple);1985.

Giga Farm; retrieved from URL http://www.virtualpet.com/vp/farm/gigapet/gpfarm/gpfarm.htm Apr. 23, 2000.

Giga Pets, 1997 [retrieved on Apr. 23, 2000], Retrieved from <URL:www.virtualpet.com/vp/farm/gigapet/gigapet.htm>.

Gordon; "Auctions Become High Tech"; Dealer Business; v29 n7; p. 21(4); Mar. 1995; Dialog: File 148, Acc#07862519.

Guiffrida, et al., Should We Pay the Patient? Review of Financial Incentives to enhance Patient Compliance:, Biomedical Journal, (1997), vol. 315, pp. 703-707.

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Australia, (Oct. 5, 1992), vol. 157, 489-491.

Horio, Hiroyuki, et al., "Clinical Telecommunication Network System for Home Monitoring", Medical & Biological Engineering & Computing, (Mar. 1994), vol. 32, 227-230.

How Flash Memory Works, Internet printout of URL address: http://www.howstuffworks.com/flash-memory4.htm, (Sep. 28, 2002), 2 pages.

Howey, et al., "A Rapidly Absorbed Analogue of Human Insulin"; Diabetes, vol. 43, Mar. 1994, pp. 396-402. (7 pages).

Hunter, "Technological Advances in Bedside Monitoring: Biosensors", Archives and Laboratory Medicine, (Jul. 1987), pp. 633-636.

Hutheesing, Nikhil, "An on-line gamble", Forbes, v157 n10 p. 288(1), May 20, 1996.

Introducing the Next Generation of About Your Diabetes, U.S. Pharmacopical Convention and American Diabetes Association, (1993).

Jaffrey et al.; "PIN: An Associated Protein Inhibitor of Neuronal Nitric Oxide Synthase"; Science; vol. 274; Nov. 1, 1996; Ref: XP 002050141.

Jimison et al., "Patient-Specific explanation in models of chronic disease", Revised Feb. 1992 Artificial Intelligence in Medicine 4 (1992) 191-205.

Jones, Chris, "Microsoft readies DocObject; technology will allow document editing in Web browsers", InfoWorld, v18 n18 p. 48(1), Apr. 29, 1996.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Kaufman, Steven, B., "The Learning Game", Nation's Business, (Nov. 1993).

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

Lachnit, Carroll, "Hawkin's Online Auction", Photo District News, vol. 16, Issue 1, p. 18, Jan. 1996.

Lacyk, John, "PCT Search Report", (Jun. 12, 1997).

Latman, N. S., "Evaluation of Electronic, Digital Blood Glucose Monitors", Biomedical Instrumentation and Technology, (1991), vol. 25, No. 1, 43-49.

Leyerle, Beverly J., et al., "The PDMS as a Focal Point for Distributed Patient Data", International Journal of Clinical Monitoring and Computing, (1988), vol. 5, pp. 155-161.

Luebke, Cathy, "Barrett-Jackson Auction Turns High-Tech", Business Journal, vol. 16, Issue 12, pp. 11, Jan. 19, 1996.

Makikawa, M., et al., "Microprocessor-Based Memory Device for Ambulatory Heart Rate and Physical Activity Recording", Methods of Information in Medicine, (1994), vol. 33, No. 1, pp. 94-96.

Marsh, David G. "Approaches Toward the Genetic Analysis of Complex Traits Asthma and Atrophy", Am. J. Respir.Crit.Care Med., (1997), vol. 156, pp. S-133-S138.

Martinez, Fernando D., "Complexities of the Genetics of Asthma", Am.J. Respir. Crit. Care Med., (1997), vol. 156, pp. S117-S122.

Marx, Wendy, "More than just the Scores: ESPNET SportsZone is a model for expanding brand names online", InformationWeek, n576 p. 61(2), Apr. 22, 1996.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

Meissner, et al., "Building an Integrated Clinical and Research Network", Proceedings of the SPIE, (Oct. 24, 1995), vol. 2618, p. 92-99.

Miles, Laughton E., "A Portable Microcomputer for Long-Term Physiological Monitoring in the Home and Work Environment", Medical Monitoring in the Home and Work Environment, (1990), pp. 47-57.

Mims; "Psychological Testing"; Computers & Electronics; v23; p. 22(6); Feb. 1985; Dialog: File 47, Acc# 2654858.

Moore, "New Applications Break Through Storage Boundaries", Computer Technology Review, (Oct. 1999), vol. 19, No. 10 p. 1.

Mule. rulebook by Electronic Arts, 1983.

Nano Baby Instructions; retrieved from file://C:\My Documents\Nano Baby Instructions.htm Apr. 23, 2000.

Nano Fighter Pets; retrieved from URL http://www.virtualpet.com/vp/farm/nano/nfighter.htm Apr. 23, 2000.

Nano Page,1997 [retrieved on Apr. 23, 2000], Retrieved from <URL:www.virtualpet.com/vp/farm/nano/nano.htm>.

Octhigotchi Instruction Manual, 1997. Dino-Kun Instruction Manual, 1997.

O'Donnell; "Alan's At It Again"; Bond Buyer; v309 n29448; p. 1(3); Jul. 21, 1994; Dialog: File 148, Acc#07478152.

Onsale Joins Fray as Online Shopping Picks Up Speed: Internet Booms; Computer Reseller News; Jun. 5, 1995; p. 73; Dialog: File 16, Acc#05649796.

ONSALE Onsale Brings Thrill of Auctions and Bargain Hunting Online; Unique Internet retail service debuts with week-long charity auction for The Computer Museum in Boston, May 24, 1995; Dialog Abstract: File 610, Acc#0489267.

Pfeiffer, E. F., "The Glucose Sensor: The Missing Link in Diabetes Therapy", Hormone and Metabolic Research, (1990), vol. 24m Suppl. pp. 154-164.

Playmates Toys deals knockout blow to virtual pet competitors with introduction of Nano Fighter™ For Boys; New Nano Pet Fighting Pet Press Release; retrieved from URL http://www.virtualpet.com/vp/farm/nano/nfightpr.htm Apr. 23, 2000.

Playmates Toys leads Americas virtual pet craze into its next generation by introducting talking Nano Pals; Talking Nano Pet Press Release; Nov. 18, 1997; retrieved from URL http://www.virtualpet.com/vp/farm/nano/talkn/tnpress.htm on Apr. 23, 2000.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Potter, David, "Fundamentals of PC-Based Data Acquisition", Sensors, (Feb. 1994), pp. 12-20.

Reis, H, "Telemedicine: Transmitting Expertise to the Point of Care Toward an Electronic Patient Record"; '97, Nashville, TN, Apr. 27-May 3, 1997, pp. 248-256, v. 3.

Research project launched to improve health of America's communities; new Disney community in Florida is focus of program. Business Wire, p10011142. Oct. 1, 1996.

Results of the world's first on-line auction, http://www.christies.com.

RO_AUCTION Auctioneers Property Database System and RO_AUCTION Auctioneers Accounting System; RO-AUCTION features; Dec. 4 1995.

Roberts; "Diabetes and Stress: A Type A Connection?", Psychology Today, (Jul. 1987), v. 21; pp. 22(1); Dialog: File 149, Acc# 05038381.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Save the earth artrock auction, http://www.commerce.com.save-earth. Auction Web, http://www.ebay.com.

Schement, "An Intelligent Controller for Neurophysiological Experiments," Proceeding of the Annual Symposium on Computer Based Medical Systems, Durham, Jun. 14-17, 1992, p. 528, line 1-p. 529, line 21.

Schenkels, P., "Supplementary European Search Report", Application No. EP 97 92 2716, (Mar. 11, 2002).

Schork, Nicholas J., "Genetics of Complex Disease", Am.J.Respir. Crit. Care Me., (1997), vol. 156, pp. S103-S109.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Seigmann;"Nowhere to Go but Up"; PC Week; v12 n42, p. A5(1); Oct. 23, 1995; Dialog: File 148, Acc#08222496.

Seybold—New Horizons teams with Duke, Real Media; The Seybold Report on Desktop Publishing, v10 n12 p. 24(1), Aug. 12, 1996.

Shandle, Jack, "Who Will Dominate The Desktop in the 90's?" Electronics, Feb. 1990, pp. 48-50. (3 pages) Cited by 2 patents.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

Skolnick et al. "Simultaneous Analysis of Multiple Polymorphic Loci Using Amplified Sequence Polymorphisms (ASPs)"; Genomics. 2: 273-279.

Soeldner, J. S., "Treatment of Diabetes Mellitus by Devices", The American Journal of Medicine, (Jan. 1981), vol. 70, 183-194.

Spitzer et al.; "The moderating effect of age on self-care"; Western Journal of Nursing Research, v18, n2, p. 136(13), Apr. 1996.

Talking Nano Puppy; retrieved from URL http://www.virtualpet.com/vp/farm/nano/talkn/talkn.htm Apr. 23, 2000.

Tamagotchi, 1997 [retrieved on Apr. 23, 2000], Retrieved from <URL:www.virtualpet.com/vp/farm/lleg/lleg.htm>.

Tandy Radio Shack , "The description of the Tandy Radio Shack TRS-80 Model 100/102 device available at http://www.old-computuers.com/musuem/computer.asp?c=233", World Wide Web, (Feb. 13, 2004), 1-3.

Telemedicine Provides Two-Way Computer Link For Parents of Very Premature Infants. PR Newswire. p1007NEM034. Oct. 7, 1996.

Theme Hospital, product review 1996 [retrieved Apr. 21, 2000], Retrieved from <URL:www.vigilante.co.uk/ep/misc/hospital.htm>.

Towards a partnership of care, M2 Presswire, Jun. 14, 2000.

United Healthcare's OPTUM Division goes online to better health by announcing a unique internet application. PR Newswire, p0801MNTH004. Aug. 1, 1996.

Updike, Stuart J., et al., "Laboratory Evaluation of New Reusable Blood Glucose Sensor", Diabetes Care, (Nov./Dec. 1998), vol. 11, No. 10, pp. 801-807.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Vallera, D. A., et al., "Accuracy of Portable Blood Glucose Monitoring", American Journal of Clinical Pathology, (1991), vol. 95, No. 2, pp. 247-252.

Virtual Pet Product Reviews, 1997 [retrieved on Apr. 23, 2000], Retrieved from <URL:www.virtualpet.com/vp/farm/reviews/reviews,htm>.

Virtual Tomagutchi, 1998 [retrieved Apr. 23, 2000], Retrieved from <URL:www.sttf.org/english/action/tomagutchi.html>.

Voelker, Rebecca, "Shoe Leather Therapy is Gaining on TB", Jama, (Mar. 13, 1996), vol. 275, 743.

Wilkins, Aaron. "Expanding Internet access for health care consumers", Health Care Management Review, Summer, Jul. 1999, 24-30.

Wyatt, J. C., "Clinical Data Systems, Part 2: Components and Techniques", Lancet, (Dec. 1994), vol. 344, No. 8937, pp. 1609-1614.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

"AdOptimizer—Ad Management Software for Websites", Newsbytes, pNEW10040041, Oct. 4, 1996.

"Blood Glucose Monitors", Portable Health Device, (1998), vol. 17(9), pp. 253-271.

"Cathay Pacific Airways-USA receives more than 1,300 bids during first five days of CyberAuction"; Business Wire, Oct. 18, 1995, p10181119.

"Cathay Pacific Airways-USA to Hold First-Ever Internet CyberAuction; CyberTravelers Can Bid for 50 Business Class Round Trips to Hong Kong—No Minimum Bid"; Business Wire; p9261084; Sep. 26, 1995; Dialog: File 148, Acc#08167091.

"Central Fetal Monitoring Systems with Optical Disk Storage", New Technology Brief, (Nov./Dec. 1998), vol. 2, No. 6, pp. 249-251.

"Digital Doggie"; retrieved from URL http://www.virtualpet.com/vp/farm/gigapet/ddoggie.htm Apr. 23, 2000.

"European Search Report", From 6858P005EP, (Mar. 27, 1998).

"Future of the Virtual Pet Industry," 1997 [retrieved on Apr. 23, 2000], Retrieved from <URL:www.virtualpet.corn/vp/ future/future.htm>.

"Giga Farm"; retrieved from URL http://www.virtualpet.com/vp/farm/gigapet/gpfarm/gpfarm.htm Apr. 23, 2000.

"Giga Pets," 1997 [retrieved on Apr. 23, 2000], Retrieved from <URL:www.virtualpet.com/vp/farm/gigapet/gigapet.htm>.

"How Flash Memory Works", Internet printout of URL address: http://www.howstuffworks.com/flash-memory4.htm, (Sep. 28, 2002), 2 pages.

"Introducing the Next Generation of About Your Diabetes", U.S. Pharmacopical Convention and American Diabetes Association, (1993).

Giuffrida, et al., Should We Pay the Patient? Review of Financial Incentives to enhance Patient Compliance:, Biomedical Journal, (1997), vol. 315, pp. 703-707.

Hunter, "Technological Advances in Bedside Monitoring: Blosensors", Archives and Laboratory Medicine, (Jul. 1987), pp. 633-636.

Latman, N.S., "Evaluation of Electronic, Digital Blood Glucose Monitors", Biomedical Instrumentation and Technology, (1991), vol. 25, No. 1, 43-49.

M.U.L.E. rulebook by Electronic Arts, 1983.

Octogotchi Instruction Manual, 1997. Dino-Kun Instruction Manual, 1997.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Poison, Gary "Recent Developments and Trends in Keychain Virtual Pets," 1997 [retrieved on Apr. 23, 2000], Retrieved from <URL:www.virtualpet.com/vp/future/trends1a.htm>.

Shandle, Jack, "Who will dominate the desktop in the 90's?", Electronics, (Feb. 1990), pp. 48-50.

Siegmann;"Nowhere to Go but Up"; PC Week; v12 n42, p. A5(1); Oct. 23, 1995; Dialog: File 148, Acc#08222496.

* cited by examiner

SYSTEM AND METHOD FOR MODIFYING DOCUMENTS SENT OVER A COMMUNICATIONS NETWORK

This application is a continuation of Ser. No. 09/540,482, filed Mar. 31, 2000, now abandoned, which is a continuation of application Ser. No. 09/394,219, filed Sep. 13, 1999, now U.S. Pat. No. 6,375,469, which is a continuation of application Ser. No. 08/814,293, filed on Mar. 10, 1997, now U.S. Pat. No. 5,951,300. All of the above named applications are incorporated herein by reference in their entirety.

FIELD OF THE INVENTION

The present invention relates generally to modifying documents sent over a communications network, and in particular to a system and method for determining the information contents of document portions and replacing undesired document portions with substitute document portions or inserting substitute document portions.

BACKGROUND OF THE INVENTION

To a large degree, the information age has been brought about by rapid advances in the field of communications and communications networks in particular. Increasingly, information which could formerly be presented in tangible, permanent media is reformatted and rendered for display on screens and monitors. Virtually any information presentable as text or text and graphics is being converted into suitable electronic messages or packets for shuttling across a communications network.

A communications network, e.g., the Internet, has an architecture in which information packets from resources or content providers is made available through service providers to users who subscribe to the service. The actual transmission takes place over the communication links of various bandwidths and types, which make up the network. Content providers typically store this electronic data on server machines connected directly to the Internet in standard format. The data is broken down into packets and these are then transmitted over the communication link. Among the diverse types of information which may be placed on the Internet in this way are articles, news briefs and updates, weather maps, books, summaries, files, software, catalogues, documents, pictorials, video files, public records, commercial literature and so forth.

Clearly, the number of packets, which can be transmitted via a communications network, is vast and varied. To aid in sorting, routing and transmitting information on the Internet the content of any given packet is usually identified by its origin (address of the content provider), a brief summary located in a conspicuous portion of the packet (e.g., in the header) or some other identification information. For example, the Internetwork Packet Exchange (IPX) protocol followed by NetWare routers, distributed by Novell, Inc., execute a so-called Routing Information Protocol (RIP) and Service Advertising Protocol (SAP). The RIP protocol involves periodic RIP broadcast packets containing all routing information known to the router. These packets are used to keep the global network synchronized. In addition, the protocol provides for periodically sending SAP broadcast packets containing all server information known to the SAP agent. Thus, the network system keeps track of the contents of the various packets to facilitate transfer, mitigate traffic problems and perform other vital operations.

In U.S. Pat. No. 5,530,852 issued to Meske, Jr. et al. the inventors disclose a method and system for receiving information in a first file written in a first markup language and identifying the information contents. The method and system ensure that even complex packets of information are processed by generating a list of profiles and topics for each list of the profiles. Secondary and tertiary files are created with anchors referencing particular information in the first file. A parsing procedure is taught by Meske to ascertain whether any information in the first file (original packet) is relevant. If so, fourth and fifth files containing the desired information are created and sent to the user.

Meske's system and method can be adapted to block or filter entire packets or portions thereof on a content-basis before performing the necessary steps to display the information—usually in the form of a page—on the user's screen. The document is later parsed to extract the profile and build additional pages to catalog and access the information. This method for building a knowledge base with embedded content profiles and in a document is useful but limited to processing the received information only.

The above-mentioned IPX protocol and similar methods, which determine the information contents of packets and use them in the routing process, can be employed to control the transfer of packets. For example, U.S. Pat. No. 5,541,911 issued to Nilakantan et al. disclose a remote smart filtering communication management system, which uses the information contents data to alleviate network traffic problems.

In particular, Nilakantan controls the traffic across a communication link between a remote network and a central device by applying forwarding rules. The resources monitor the characteristics of the forwarded data packets received across the communication link to learn characteristics of the users of the remote network. In response to the learned characteristics, the resources generate link management messages and forward these to the remote interface. The remote link management resources in the remote interface are responsive to the link management messages and tailor the forwarding rules to the user characteristics. The packets can now be filtered or blocked based on user characteristics.

The use of selective blocking and filtering of packets by Nilakantan et al. is applied to ultimately reduce network traffic. The present invention is centered on sending management messages, which are then used to optimize packet traffic across given links in the network. In other words, the problem addressed by this invention is the high volume caused by the proliferation of packets on the network.

Blocking and filtering of packets or their parts can be employed to speed up the page rendering process on the user's screen. For example, blocking functions may restrict packets from a list of providers or an entire block of providers from ever being sent to the user. This feature allows one to prevent undesired packets (e.g., packets containing pornographic material) from being sent to the user and rendered on his or her screen. Filters can be preset to choose packets based on the time they require for rendering or in accordance with other user-specified standards (e.g., information contents). Proper application of these two functions results in an optimized and personalized page rendering procedure.

In the most common practical scenario, however, a network user sends a direct request for an entire document from a terminal located on his or her premises to the service provider. The provider verifies whether the document is already stored in local memory and, if not, obtains this document from the content provider. While the user's request is processed the service provider usually passes on to the user a number of unsolicited document portions, e.g., document portions from other service providers such as advertisement servers. Thus, subscribers receive, in addition to the requested document(s), numerous other document portions of varying degrees of interest, importance, or indeed, annoyance to them. When the page is rendered on the user's screen these embedded document portions, despite the fact that they are unsolicited and often undesirable, are relentlessly displayed as a part of the document.

Under these circumstances, what is needed is a system and method for modifying or substituting undesired document portions, because blocking and filtering functions performed on the packet level don't allow for portions of a document to be sent with desired content in place of the portions of undesired content. For example, the service provider, the user or another party may wish to exchange or modify a document being sent to the user. This situation may occur when the service provider wishes to enclose vital information with the document requested by the user. The use of the bandwidth allocated to a less important document portion, hence a document portion swap, would be highly appropriate for this purpose. In another situation, the user may wish to block undesired document portions. For instance, when recording television programming on the VCR recorder the user can selectively block advertising material from being recorded. Analogously, when rendering a web page the user may wish to omit specific document portions from being rendered on the page.

At the present time the problems associated with this type of document modification have not been addressed, much less solved. Consequently, what is needed is a system and method, which solves the problems associated with document modification based on the information contents in a communications network such as the Internet.

SUMMARY OF THE INVENTION

In view of the above, it is an object of the present invention to provide a system and a method for modifying documents in a communications network, by replacing an original document portion with a substitute document portion or inserting a substitute null document portion. The replacement decision is made based on the information content of the original document portion.

It is another object of the invention to perform this exchange operation in an efficient manner in a convenient part of the network and to allow the network user to decide which document portions should be exchanged.

Yet another object of the invention is to perform the document modification according to decisions derived from the service provider.

Still another object of the invention is to ensure that the system and method of invention can be integrated in any communications network in which content providers, service providers and users are connected via communication links (e.g., the Internet).

Still further another object of the invention is to detect and replace confidential content that appears in the original document with desired content.

Still yet another object of the invention is to detect and replace junk mail, viruses or confidential content that appears in received data packets.

These and other objects and advantages will become more apparent after consideration of the ensuing description and the accompanying drawings.

The objects and advantages of the invention are ensured by a system and method applied to a communications network, which transmits information in the form of documents or rather, document portions, e.g., the Internet. An original document is modified to produce a modified document based on the original document portions and, specifically, based on an identifier portion and an information portion of each original document portion. A substitute document portion is inserted in the place of each undesired original document portion. The system according to the invention provides for a number of content providers whose servers transmit documents or document portions on the network. Service providers relay these document portions to a given network user, who displays them on a user set, e.g., a computer or a television set.

The system has a controller, typically a proxy server, for parsing the original document to locate the identifier portion of each of the original document portions, determining the information portion of each original document portion to identify the undesired original document portion, i.e., an original document portion which has an undesired content, and issuing a swap order the undesired original document portion is found. For instance, the undesired content may be an advertisement or a message not relevant to the information, which the user desires to view on his or her user set.

A substitute document server receives the swap order and sends the substitute document portion to the controller. A swapping device or mechanism inserts the substitute document portion in place of the undesired original document portion. At this point the substitute document portion can be passed on to the user set and displayed. Depending on the communications network and user preferences, the actual display set can be a computer, a television set, or any other suitable end terminal with a display screen.

In one version of the system according to the invention the controller is located on the premises of the user, i.e., at the user's residence or at his or her work place. Advantageously, in this embodiment the controller can be integrated with the user set. It is also possible to integrate the swapping mechanism with the controller. Of course, the controller can also be located on the premises of the service provider and be integrated with the swapping mechanism there. In this situation the role of the controller and swapping mechanism can be most efficiently performed by the proxy server.

The identifier portion of any original document portion can be as simple as a network address. In general, this will be the network address of the content provider who placed the document portion on the network. (Address-based identification is one of the most common ways of identifying document portions.) The content of the information portion can be easily determined as desired or undesired from the provider's address. For this purpose, the controller should have in its memory or some other accessible storage resources a list of network addresses of content providers. In another embodiment the identifier portion will have a brief description or designation of what is contained in the information portion. Such identifier portion will generally consist of any number of signs and/or characters (usually abbreviations).

In a preferred embodiment the controller has a device or mechanism for matching the dimensions of the substitute document portion with the dimensions of the original document portion being replaced, i.e., the undesired original document portion. This provision ensures that the swapped information will be of appropriate size when rendered on the user's screen, thus preserving the page layout, which would have been obtained without swapping.

A further embodiment adds to the system a user profile bank. The bank has user profile information, e.g., statistical information, personal preferences or any other information either compiled or gathered directly from the user. The profile information is delivered to the controller such that the swap order can be issued based on the user's preferences to tailor the substitute document portions to the user's needs or other relevant profile information.

The system of the invention can be used in any communications network having the general architecture described. As mentioned above, the Internet is well suited for the system of the invention. The method of swapping undesired original document portions with substitute document portions is practiced in communications network exhibiting the same architecture as required for the system.

A detailed description of the system and method of the invention are set forth below in reference to the drawing figures.

DETAILED DESCRIPTION

Figure 1:
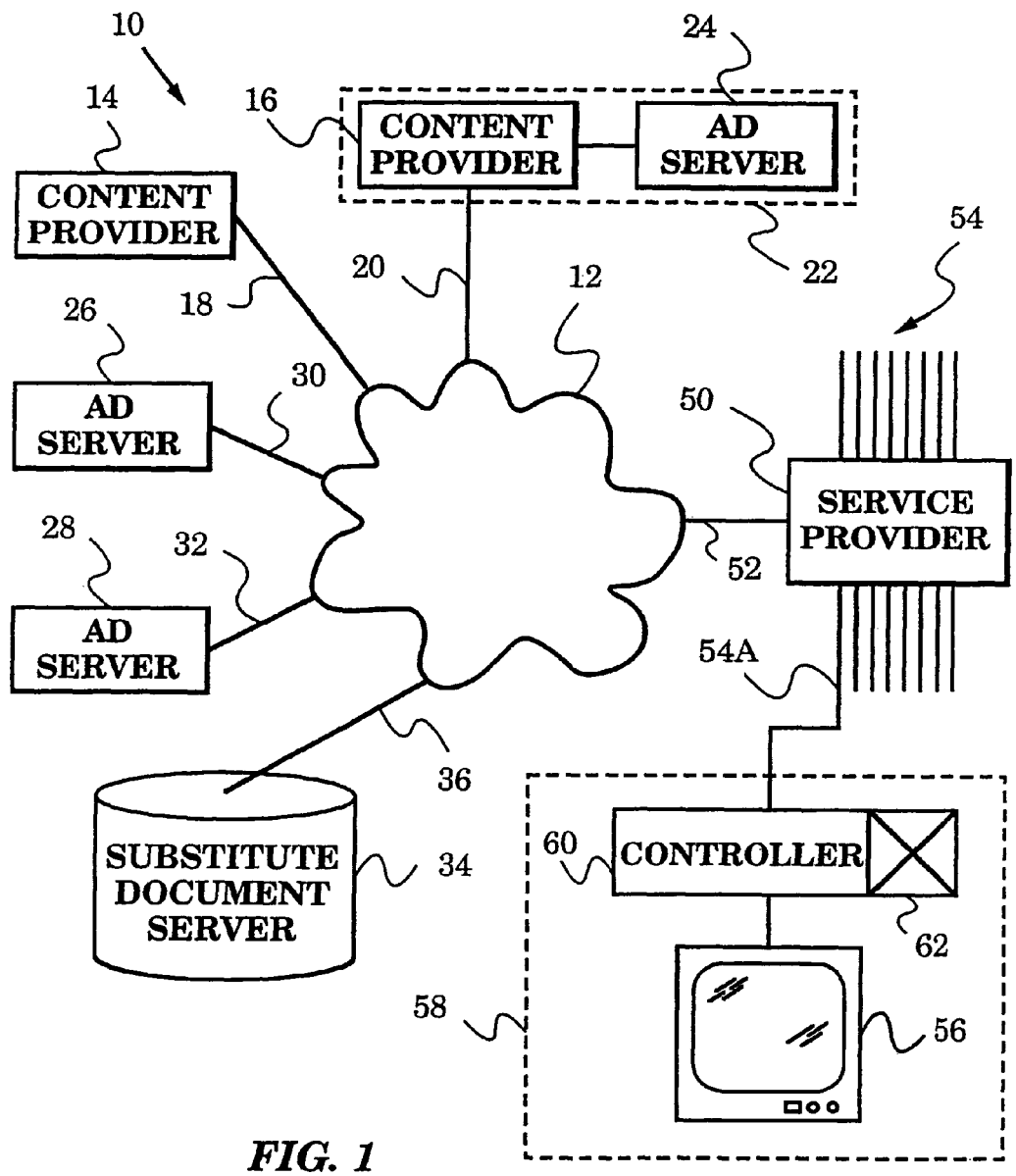
FIG. 1 is a block diagram of one embodiment of the system of invention.

An advantageous embodiment of the invention is illustrated in the block diagram of FIG. 1. A document modification or swapping system 10 possessing the necessary architecture to practice the invention is built around a communications network 12. The individual links and resources of network 12 are not shown, but are generally known to include couplings, high and low bandwidth links, filters, power sources, repeaters, transformers, up- and down-converters, amplifiers and any number of other equipment required to efficiently transmit information across large physical distances. Network 12 may be a stand-alone network or one which takes advantage of existing connections and resources, e.g., telephone lines. In the preferred embodiment network 12 is simply the Internet.

Two content providers 14, 16 are connected to network 12 via communication links 18 and 20 respectively. Any suitable medium of sufficient bandwidth to transmit the required information to and from network 12 can be used as links 18, 20. Content providers 14, 16 are servers equipped with the necessary resources to transmit and receive information, specifically requests or queries for the contents of their data banks (not shown). Typically, content providers 14, 16 have information such as articles, news briefs and updates, weather maps, books, summaries, files, software, catalogues, documents, pictorials, video files, public records, commercial literature and so forth.

Provider 14 is an independent server, while provider 16 is a part of a larger resource 22 including an advertisement server 24 (hereafter "ad server"). Although it is understood that either provider 14 or 16 may place on network 12 various types of information, e.g., requested files, non-requested information, undesired information and advertising material, the distinction between ad server 24 and provider 16 is useful for better illustrating the operation of system 10. Thus, in the present embodiment it will be assumed that ad server 24 places, via provider 16, on network 12 unsolicited information, i.e., commercials and advertisements, while provider 16 delivers requested and/or desired information.

System 10 also has dedicated ad servers 26 and 28 which deliver to network 12 via communication links 30 and 32 commercials and advertisements in the broadest sense.

A substitute document server 34 is connected with network 12 by communication link 36. Server 34 contains information which is not requested or solicited but is desirable or useful. For example, server 34 may contain health-related information, warnings, general advisories and many other types of information.

Figure 2:
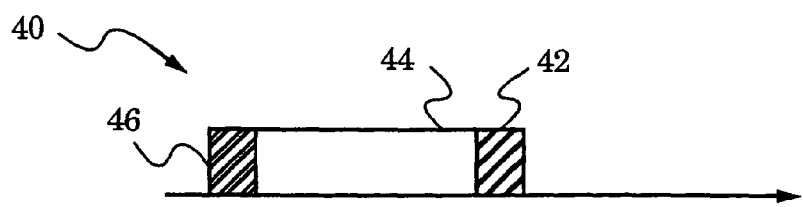
FIG. 2 is a diagram of a document portion.

The different types of information placed on network 12 by providers 14, 16, ad servers 24, 26, 28 and substitute document server 34 are formatted in documents or document portions such as document portion 40 shown in FIG. 2. It is understood that the fundamental building blocks of document portion 40 are information packets (not shown). Although the detailed structure of document portion 40 will be adapted to network 12 each document portion 40 has the same general make-up. A header or an identifier portion 42 generally precedes an information portion 44 with the actual information content. In some cases a footer 46 may be provided to designate the end of document portion 40. Frequently, identifier portion 42 is simply the network address of the server, which placed document portion 40 on network 12. Alternatively, identifier portion 42 contains a designation or identification of the information contained in portion 44. Examples of different forms which identifier portion 42 can assume when network 12 is the Internet are discussed below.

A service provider 50 is in communication with network 12 via communication link 52. Typically, service provider 50 will have numerous lines 54 connecting directly to the subscribers or network users. In particular, line 54A establishes a link between service provider 50 and a user set 56 on user premises 58. When network 12 is the Internet user set 56 is a computer or a network unit. Other devices such as television sets or display devices capable of receiving and/or sending document portion 40 can be used as well. A person of average skill in the art will be able to ensure a suitable connection of user set 56 with service provider 50.

A controller 60 is switched between user set 56 and service provider 50. Controller 60 is capable of reading identifier portion 42 of a document portion 40 to determine the content of information portion 44. A swapping device 62, preferably integrated with controller 60 as shown, is also provided to receive a swap order which controller 60 issues when information portion 42 of a packet 40 has an undesirable content.

Figure 4:
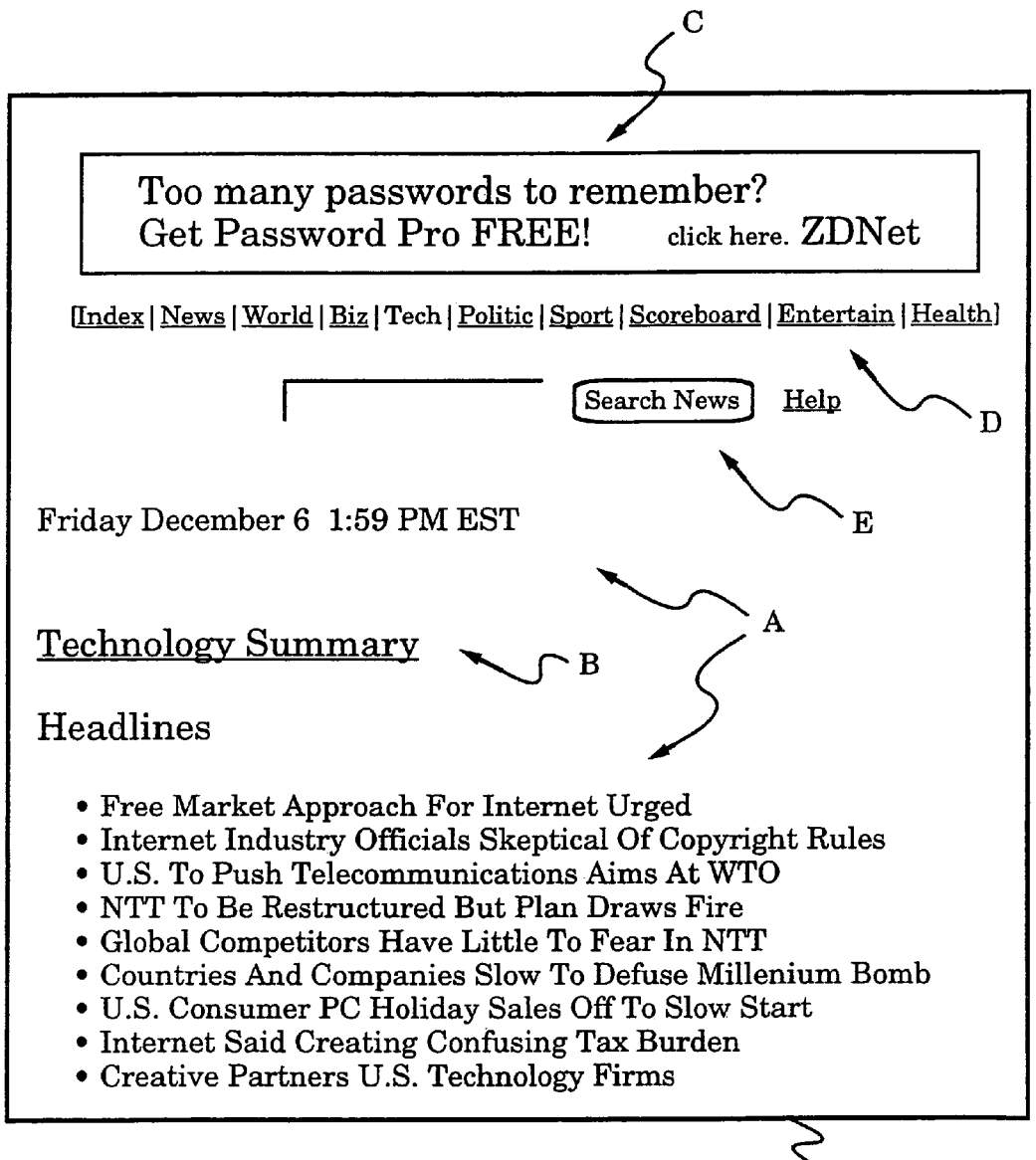
FIG. 4 is an example screen display on a user's set.

The operation of system 10 is now described for the case in which network 12 is the Internet. As an example, FIG. 4 shows a screen display or a page 70 on user set 56. Page 70 is actually constructed from a number of original document portions analogous in all respects to document portion 40. The below listing identifies how the page is rendered from original document portions A, B, C, D and E. The formats used conform to the widely accepted and well-known hypertext mark-up language (HTML).

Example Page

HTML for document portion A:

Friday December 6 1:59 PM EST
</strong>
<!--Text Start-->
<p>
<h2><a href=/headlines/961206/tech/summary_1.html>Technology Summary</a></h2>
<hr>
<h2>Headlines</h2>
<ul>
<li>< a href=/headlines/961206/tech/stories/free_1.html><b>Free Market Approach For Internet Urged</b></a>
<li>< a href=/headlines/961206/tech/stories/copyright_3.html><b> Internet Industry Officials Skeptical of Copyright Rules</b></a>
<li>< a href=/headlines/961206/tech/stories/telecom_1.html><b>U.S. To Push Telecommunications Aims At WTO</b></a>
<li>< a href=/headlines/961206/tech/stories/ntt_1.html><b>NTT To Be Restructured But Plan Draws Fire</b></a>
<li>< a href=/headlines/961206/tech/stories/nttanalysis_1.html><b> Global Competitors Have Little To Fear In NTT</b></a>
<li>< a href=/headlines/961206/tech/stories/millennium_1.html><b> Countries And Companies Slow To Defuse Millennium Bomb</b></a>
<li>< a href=/headlines/961206/tech/stories/sales_1.html><b>U.S. Consumer PC Holiday Sales Off To Slow Start</b></a>
<li>< a href=/headlines/961206/tech/stories/taxes_1.html><b>Internet Said Creating Confusing Tax Burden</b></a>
<li>< a href=/headlines/961206/tech/stories/creative_1.html><b>Creative Partners U.S. Technology Firms</b></a>
</ul>
</body>
</html>

HTML for document portion B:

<html>
<head>
<title>Technology Summary</title>
</head>
<body>

HTML for document portion C (Advertisement):

<!-- AdSpace -->
<!-- AdParam        yhn000001424187 -->
<center><p><a href="http://www.yahoo.com/SpaceID=yhn00000142/AdID=4187/?http://community.zdnet.com/register/register.cgi"><img width=460 height=55 src="http://www.yahoo.com/adv/zdi2/password5.gif" alt="[Too many passwords to remember? Download Password Pro for free.]" border=0></a><p></center>
<!-- AdSpace -->

HTML for document portion D (Links):

<center><strong>[<a href=/headlines/>Index</a>|
<a href=/headlines/news/>News</a>|
<a href=/headlines/international/>World</a>|
<a href=/headlines/business/>Biz</a>|
<strong>Tech</strong>|
<a href=/headlines/politics/>Politic</a>|
<a href=/headlines/sports/>Sport</a>|
<a href=http://sports.yahoo.com/>Scoreboard</a>|
<a href=/headlines/entertainment/>Entertain</a>|
<a href=/headlines/health/>Health</a>
]</strong>
</center>
<p>

HTML for document portion E (Processing User Input):

<center>
<form method=get action="http://search.main.yahoo.com/search/news">
<hr>
<input size=24 name=p> <input type=submit value="Search News">
<input type=hidden name=n value=10>
<a href="http://www.yahoo.com/docs/info/news_search_help.html">
<small>Help</small></a><br>
</form>
</center>
<!--StartLinks-->

-continued

<!--EndLinks-->
<hr>
<strong>
<!-- Yahoo Time Stamp: 849898740 -->

In the above example original document portions A, B, C, D and E correspond to those indicated in FIG. 4. The information rendered and displayed on page 70 is of the news type and it is understood that any other type of information can be involved. Original document portion C contains an ad, which originated in one of ad servers 24, 26 or 28 and was not requested by the user. Specifically, document portion C starts with identifier portion 42 indicating that the information to follow is an ad.

<!—AdSpace—>

In an alternative case, identifier portion 42 can legitimately contain:

<a href=http:..www.yahoo.com/SpaceID=yhn00000142/AdID=4187/?http://community.zdnet.com/register.cgi">

Here, portion 42 identifies the network address of ad server (24, 26 or 28). It is clear that a number of commands are required to render document portion C. These commands relate to proper spacing, location and other parameters of document portion C. The format of these commands is commonly known and widely used, e.g., in the layout of home pages for Internet users. A person of average skill in the art will know how to interpret the commands and how they act to render document portion C on user set 56.

During operation the network user will send requests from user set 56 to service provider 50 for specific information, e.g., |Biz| in section D. Service provider 50 will, based on this request, obtain the desired information from content provider 14 or 16 (depending on which provider has the information). Of course, service provider 50 may have already downloaded the information in question. This may be the case with frequently asked for data, minute-by-minute updates, etc. In such situation provider 50 can comply with the request without looking for the information on network 12. In any case, however, the requested information originates at provider 14 or 16.

Figure 5:
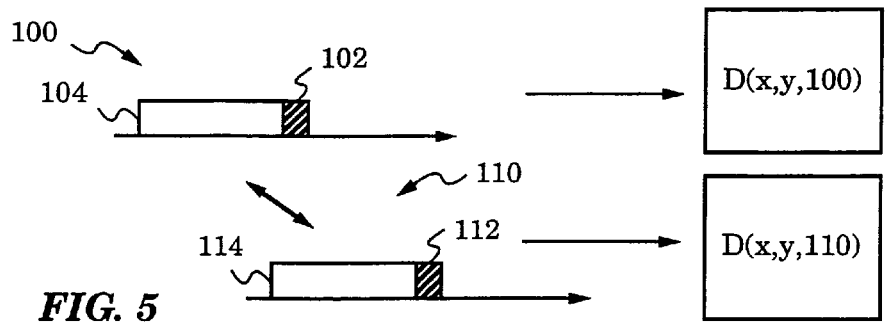
FIG. 5 is a diagrammatic representation of an original document portion and a substitute document portion.

The document as finally rendered on the screen of user set 56 thus consist of many document portion such as portion 40. As shown in FIG. 5, the specific document portion requested by the user is referred to as original document portion 100 for clarity. After original document portion 100 is obtained from provider 14 or 16 (or retrieved from the memory resources (not shown) of service provider 50) it is transmitted via line 54A to controller 60. An identifier portion 102 of original document portion 100 is read by controller 60 to determine the content of information portion 104 of original document portion 100.

As explained above, an ad from ZDNet, which is considered undesirable content, has identifier portion 102 describing the information to follow as <!--AdSpace-->. Alternatively, identifier portion 102 may simply contain the network address <a href="http://www.yahoo.com/SpaceID=yhn00000142/AdID=187/?http://community.zd-net.com/register/register.cgi"> of ad server (24, 26 or 28, depending on which server placed the ad on network 12). Controller 60 has properly received from user set 56 the request |Biz|. While parsing the original document obtained as a result of the request controller 60 detects identifier portion 102 of original document portion 100 (in this case the same as document portion C described above) which contains <!--AdSpace-->. These characters distinctly signal that the information in original document portion 100 is an undesired original document portion (in this case unsolicited). Consequently, controller 60 will issue a swap order to swapping mechanism 62.

Figure 6:
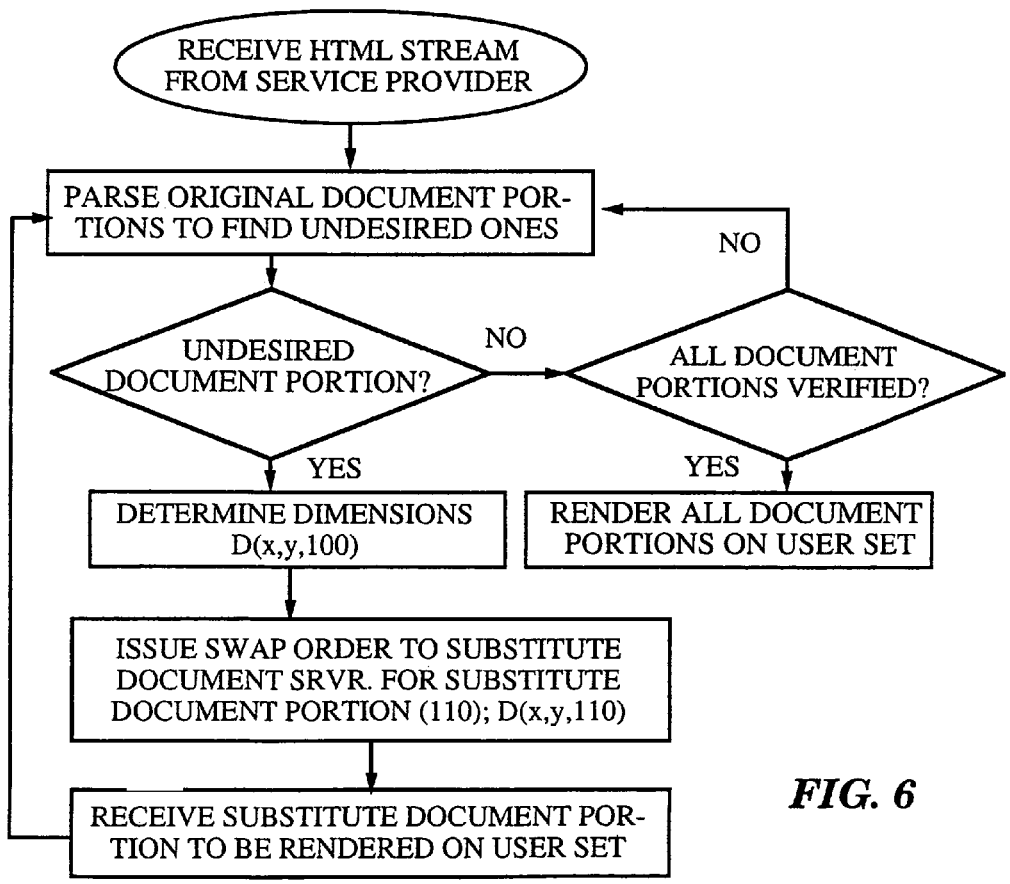
FIG. 6 is a flow diagram showing how a swap order is issued.

The swap order is formatted as any other information request (e.g., the one for |Biz|) and is addressed to substitute packet server 34. FIG. 6 shows of flow diagram detailing the steps involved in generating and issuing the swap order. It is understood that the software for executing these steps can be written by any person skilled in the art.

The swap order travels via line 54A to service provider 50 who procures the requested substitute document portion 110 (see FIG. 5) from substitute document server 34. Substitute document portion 110 has dimensions D(x,y,110) when rendered as show in FIG. 5. Preferably dimensions D(x,y,110) are close or equal to dimensions D(x,y,100) of original document portion 100. This provision will ensure that page 70 on the user set 56 will have approximately the same size as if original document portion 100 had been received and rendered on the screen of user set 56. In many cases this request can be easily satisfied since the size and width of any document portion when rendered is generally provided as a rendering hint and can be read directly from the HTML code. In the above example original document portion C includes the hint: <img width=460 height=55. In other cases controller can either fetch the content of original document portion 100 to determine the rendered size.

Alternatively, when identifier portion 102 contains the address <ahref=http://www.yahoo.com/SpaceID=yhn00000142/AdID=4187/?http://community.zdnet.com/register/register.cgi> controller 60 will be alerted that the information in original document portion 100 is undesired. That is because controller 60 keeps a list of addresses of content providers or ad servers or both. By comparing the address of portion 102 with the addresses of providers 14, 16 controller can ascertain that information portion 104 is undesirable, since the address of zdnet (one of ad servers 24, 26 or 28) is not on the list. If controller 60 is working with a list of ad servers 24, 26 or 28 it will determine that information portion 104 is undesirable when identifier portion 102 contains the address of one of ad servers 24, 26 or 28. Clearly, when using the address-based method of identifying undesirable information the address lists should be updated frequently. At this point, controller 60 will issue a swap order, as described above, to swapping mechanism 62. The swap order will be used, as explained above, to procure substitute document portion 110 from substitute document server 34. Again, it is preferable that dimensions D(x,y,110) of substitute document portion 110 be approximately equal to dimensions D(x,y,100) of original document portion 100.

Figure 3:
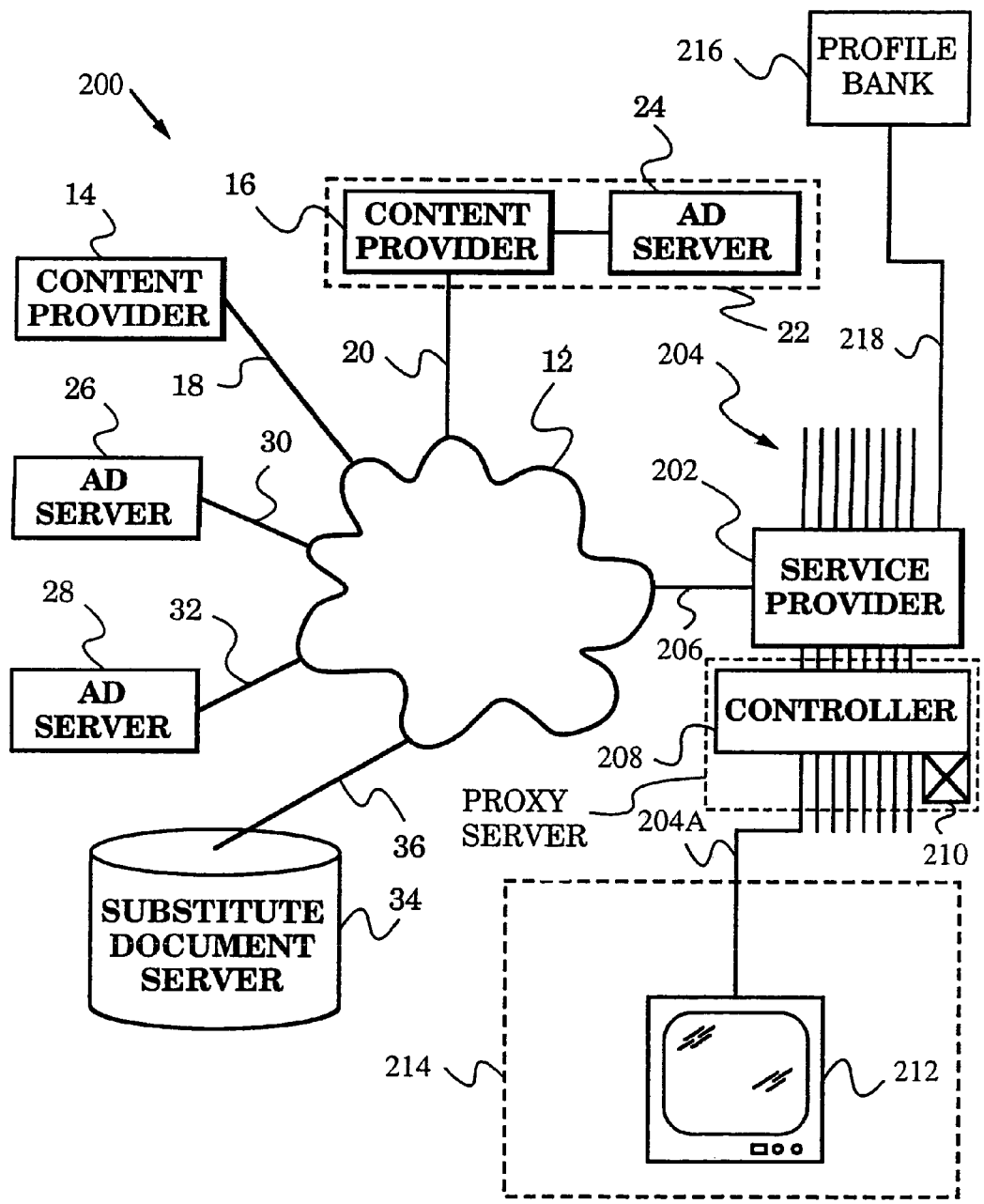
FIG. 3 is a block diagram of another embodiment of the system of invention.

Another embodiment of the invention is shown in FIG. 3. As in the first embodiment, a document modification system 200 consists of content providers 14, 16, ad servers 24, 26, 28 connected to network 12 by communication links 18, 20, 30 and 32. Substitute document server 34 is connected to network 12 by link 36.

A service provider 202 with lines 204 going out to subscribers is connected to network 12 via link 206. A controller 208, most conveniently a proxy server, is connected directly to a number of lines 204 on which the document portion swapping or insertion function is desired. Controller 208 may be integrated in the circuitry of service provider 202 or be a stand-alone unit. A swapping mechanism 210 is connected to controller 208 and, in a particularly convenient embodiment, can be integrated with the circuitry of controller 208 and service provider 202. The choice of how service provider 202, controller 208 and swapping mechanism 210 are arranged and interconnected can be determined by the circuit designer. In fact, if service provider 202 has all the necessary hardware and circuitry then the functions of controller 208 and/or swapping mechanism 210 may all be performed by service provider 202 given the appropriate software.

A particular line 204A shows the path from service provider 202 to user set 212 on user premises 214. In this embodiment no additional equipment is required of the user. This means that user set 212 is simple to install and may, for example, be a television set configured for WebTV or OpenTV.

A profile bank 216 is also connected via line 218 to service provider 202. Bank 216 typically contains user information such as user preferences, past activity data or even medical records. The connection with bank 216 is such that service provider 202 may request and obtain user profile information from bank 216.

The operation of this embodiment is analogous to that of the first embodiment. The difference is that the functions of parsing original document and specifically original document portions 100 and deciding whether to issue a swap order for substitute document portion 110 are performed by service provider 202. In addition, when issuing the swap order, swapping mechanism 210 may take into account the profile of the user obtained from bank 216.

For example, data bank 216 may contain the medical records indicating that the user is a diabetic and should be reminded to monitor their blood glucose level. In this situation, when original document portion 100 is undesired, swapping mechanism 210 will issue a swapping order addressed to substitute document server 34 to provide a substitute document portion 110 in which information portion 114 contains the message "remember to monitor your blood glucose level". In the event the user is trying to quit smoking, substitute document portion 110 may contain the following message: "Don't give up! You can quit smoking!". In the event the user succumbs easily to advertisements, substitute document portion 110 may contain no information; i.e. a substitute null document portion. The substitute null document portion is preferably stored at the controller 60, but could also be stored at a location coupled to the controller 60, such as the substitute document server 34. Alternatively instead of replacing the undesired document portion, the advertisement is not displayed or deleted, if already stored within the system 58, by the controller 60 with nothing inserted in its place.

Figure 7:
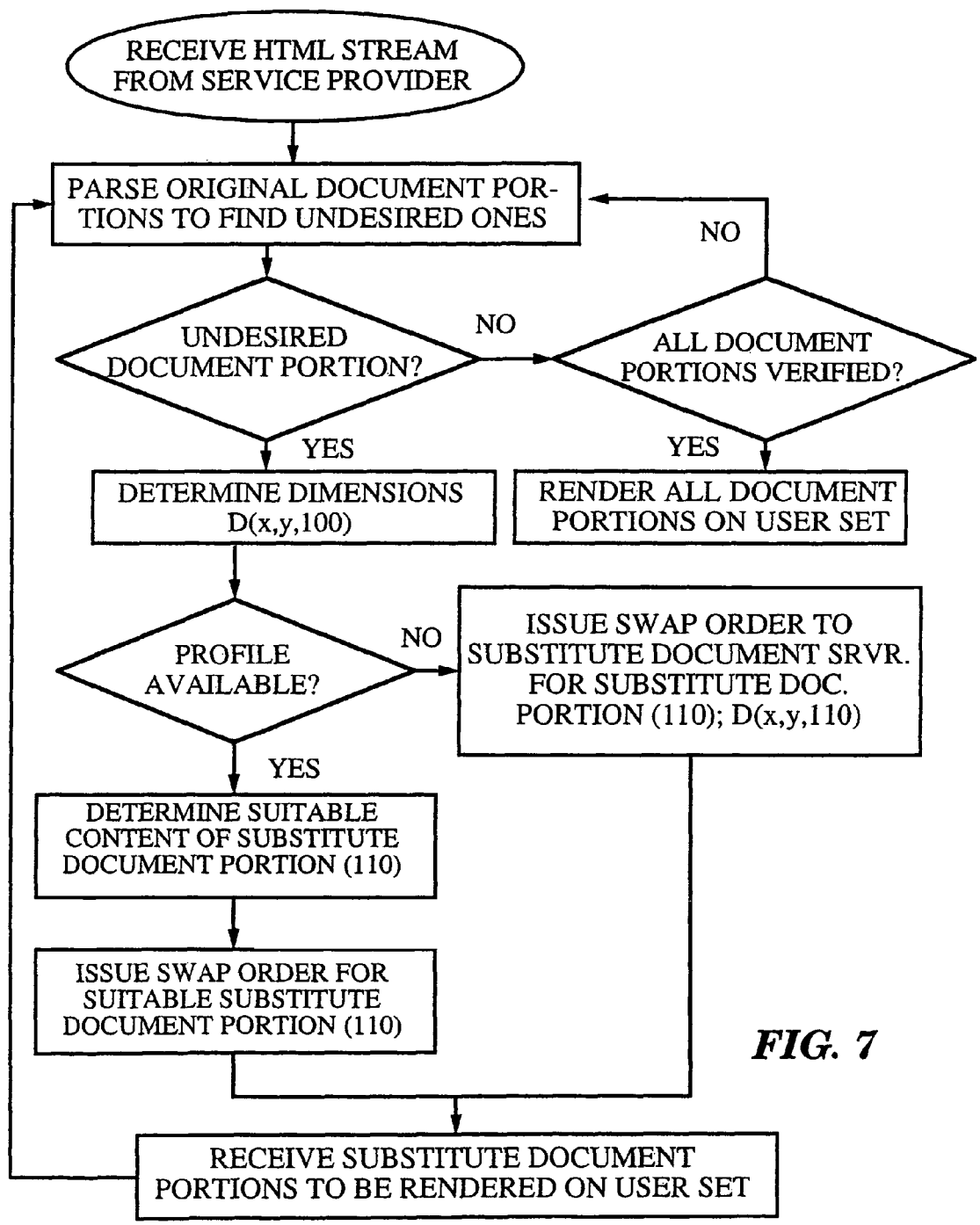
FIG. 7 is a flow diagram showing how a swap order is issued when profile bank information is available.

FIG. 7 shows in flow diagram format how the swap order is generated and issued. Swapping mechanism 210 and controller 208 will perform these steps with the aid of conventional software steps, which can be programmed by a person skilled in the art.

In a preferred embodiment of the invention system 10 is used in conjunction with a browser software installed on user set 56. Browsers are well known and commonly used to communicate on the Internet. Examples of suitable browsers include the Netscape Navigator© supplied by Netscape, Inc. and Internet Explorer© provided by Microsoft, Inc. The operation of all components is as described above with the difference that the browser software performs the function of controller 60 and swapping mechanism 62 according to the diagram of FIG. 6.

For example, the user may wish to be updated on the local news rather than receive advertisements. In this case the user will select under the options "what to swap" to receive information content 114 concerning local news.

Alternatively, the user may wish to be reminded of other important personal information. For example, the user may have asthma. He or she will then select substitute document portion 110 to contain a reminder to take their respiratory peak flow reading or appropriate medication. Clearly, the information can be tailored to any user according to need. To offer these options substitute document server 34 has to be loaded with the appropriate information.

Figure 8:
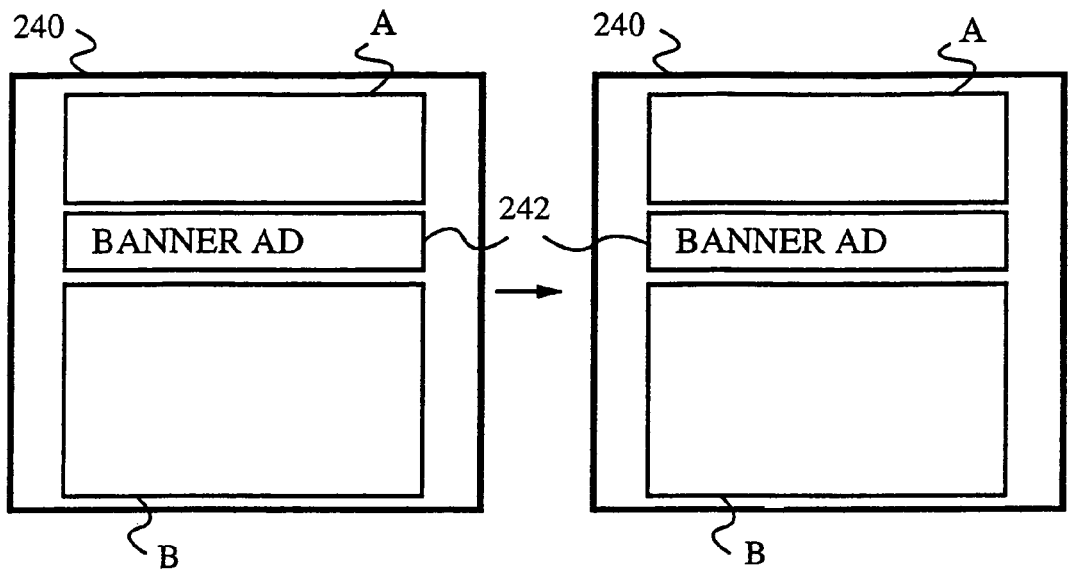
FIG. 8 is a diagram illustrating typical placement of undesired original document portions on a page.
Figure 9:
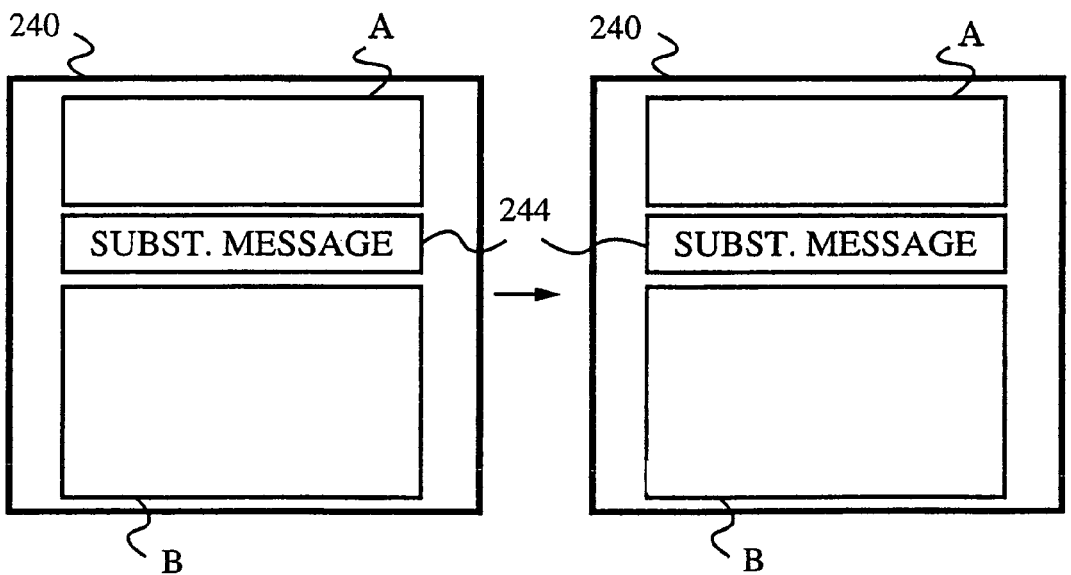
FIG. 9 is a diagram illustrating the replacement of undesired original document portions with specified substitute document portions.

In a particularly advantageous embodiment of the invention the browser can be instructed to replace all banner ads. These ads are located using the techniques discussed above. Two typical web pages 240 with banner ads 242 are shown in FIG. 8. Ads 242 are located in the middle of each page 240 between sections A and B. The browser will easily recognize and swap these ads with substitute document portions, which render to messages 244 as shown in FIG. 9.

In an embodiment adapted to current practice controller 60 or 208 can even determine where an address of an identifier 102 is directed to by going to that address. This has to be done when ad servers require the user to "click" on them to go to a web page, which describes the item. In most cases the "click-through" web page is hosted on a different service. As the page is being rendered, controller 60 or 208 operating according to the method of the invention can determine whether each HREF instruction goes by looking up network addresses as registered in the Domain Network Server (DNS). An HREF which is part of an image that is associated with a different address than the source HTML from content provider 14, 16 is usually an advertisement.

Many ad services keep track of "click-through" rates. This is done by aliasing an address on the current service, which bounces the click to the target address. In this way the service can count how often the alias was used. The method of invention can be adapted to this situation in two ways.

According to a first strategy, the reference can be identified by making an HTTP request from the HREF address and then looking at the reply address. If a redirect to another site is discovered then the document portion most likely contains an advertisement.

A second strategy is to parse the HREF string. In the listing shown above the redirect address contained in original document portion C is easy to find; it is: href="http://www.yahoo.com/SpaceID=yhn00000142/AdID=4187/?http://community.zdnet.com /register/register.cgi">. Although the request is part of the "yahoo.com" address, the redirect goes to "community.zdnet.com". A DNS lookup of this address reveals that it belongs to a different service and that document portion C is an ad.

Finally, the swapping function according to the invention can be used as an insert function. For example, if original document portion 100 contains a blank, controller 60, 208 can send a request for substitute document portion 110 to fill this blank. In this manner the space on the rendered page is more completely and efficiently utilized.

In an alternate embodiment, any data packet or document received by the controller 60 from the network 12 and service provider 50 is checked for unwanted content. Examples of unwanted data packet content include junk mail, viruses and unrequested confidential material. If there exists unwanted content, it is deleted or replaced by desired content or by a null content. For example, the data packet may include confidential medical information or reports for a patient that does not correspond to the patient associated with the system 58 that received the data packet. In one embodiment, the controller 60 scans the contents of the received data packet and compares the scanned content to information that identifies the user of the system 58 or to a list of unwanted content topics that received the data packet. If a portion of the data packet does not correspond to the information that identifies the user of the system 58 or corresponds to an item in the list of unwanted content topics, a swap order for that portion is generated and a swap is issued. The swap order is sent to the swapping mechanism 62 to retrieve substitute content that is then inserted in place of the unwanted portion of the data packet similar to an advertisement replacement. The swap order also could request a null portion or data packet containing no information that is inserted in place of the unwanted portion of the data packet. Examples of items in the list of unwanted content topics are junk mail or virus information.

In another embodiment, the system can prevent the display of misdirected email contents or email attachments. For example, the controller 60 checks or parses the contents of an email data packet and compares the checked or parsed contents against the list of unwanted content topics. For example, the confidential content may include confidential medical information or reports intended for delivery to a different location.

The swap order is formatted and addressed to the substitute document server 34. The swap order travels to service provider 50. The service provider 50 procures the requested substitute document portion from the substitute document server 34. Once the substitute document portion is sent by the substitute document server 34 to the controller 60, the swapping mechanism 62 inserts or replaces the undesired data packet with the substitute document portion received from the substitute document server 34.

Although the above description contains many specificities, these should not be construed as limitations on the scope of the invention but merely as illustrations of the presently preferred embodiment. Many other embodiments of the invention are possible. For example, the functionality of the controller and swapper may reside in software installed on the service provider's resources. Alternatively, software resident in the user set may cooperate with software in the service provider's resources to provide the functionality of the controller and swapping mechanism.

Therefore, the scope of the invention should be determined not by the examples given but by the appended claims and their legal equivalents.

What is claimed is:

1. A system for displaying a document to a user, the system comprising:
   a profile bank storing a user profile including medical information about said user;
   a substitute document server storing personalized content comprising health-related information;
   a user set configured to display documents; and
   a controller configured (a) to retrieve original content in a document from an original content provider, (b) to retrieve with the user profile, and (c) to generate a modified version of the document by replacing at least a first portion of the original content in the document with a second portion of the personalized content received from the substitute document server based upon the medical information about the user, wherein the first portion of the original content in the document is modified using the second portion of the personalized content to generate the modified version of the document prior to display of the modified version of the document to the user via the user set, wherein the first portion of the original content in the document that is replaced is selected based upon an identifier in the original content.

2. The system of claim 1, wherein the document comprises data packets.

3. The system of claim 1, wherein the user set comprises a computer.

4. The system of claim 1, wherein the user set comprises a television.

5. The system of claim 1, wherein the second portion of personalized comprises a behavior modification message.

6. The system of claim 1, wherein the second portion of the personalized content comprises information corresponding to a medical condition of the user.

7. The arrangement of claim 1, wherein the first portion of the original content in the document that is modified is selected based upon an address in the original content.

8. The arrangement of claim 1, wherein the substitute document server is located remotely from the original content provider, the profile bank and the user set.

9. The arrangement of claim 1, wherein the personalized content further comprises health-related warnings and advisories.

10. The arrangement of claim 1, wherein the personalized content comprises information not requested or solicited by the original content.

11. A method of modifying content in a document, comprising:
  comparing original content in a document received from an original content provider with a stored user profile to identify at least a first portion of original content that is undesirable based upon the user profile, wherein the user profile includes medical information about a user;
  requesting a second portion of personalized content comprising health-related information from a substitute i0 document server based upon said medical information about said user;
  generating a modified version of the document by modifying at least the first portion of the original content in the document with the second portion of personalized content received from the substitute document server in response to the request; and
  providing the modified version of the document to a user set that displays the modified version of the document to the user, wherein the first portion of the original content in the document that is modified is selected based upon an identifier in the original content.

12. The method of claim 11, wherein the document comprises data packets.

13. The method of claim 11, wherein the user set comprises a computer.

14. The method of claim 11, wherein the user set comprises a television.

15. The method of claim 11, wherein the second portion of personalized content comprises a behavior modification message.

16. The method of claim 11, wherein the second portion of personalized content comprises information corresponding to a medical condition of the user.

17. The method of claim 11, wherein the first portion of the original content in the document that is modified is selected based upon an address in the original content.

18. The method of claim 11, wherein the second portion of personalized content is requested and received from the substitute document server via the Internet.

19. A system for displaying a document to a user, the system comprising:
  a profile bank storing a user profile including medical information about said user;
  a substitute document server storing personalized content comprising health-related information;
  a user set configured to display documents; and
  a controller configured to (i) retrieve original content in a document received from an original content provider and the user profile from the profile bank, and parse by parsing the document to locate at least one of an identifier portion and an information potion of each portion of document, (ii) request one or more portions of the personalized content based upon said medical information about said user, (iii) generate a modified version of the document by replacing at least one portion of the original content in the document with the one or more portions of the personalized content received from the substitute document server in response to the request, and (iv) display the modified version of the document to the user using the user set, wherein a first portion of the original content in the document that is replaced is selected based upon the identifier portion in the original content.

20. A method of modifying content in a document, comprising:
  retrieving original content in a document from an original content provider and a stored user profile and, parsing the document to locate at least one of an identifier portion and an information potion of each portion of the document, wherein the user profile includes medical information about a user;
  requesting one or more portions of personalized content comprising health-related information from a substitute document server based upon said medical information about said user;
  generating a modified version of the document by replacing at least one portion of the original content in the document with the one or more portions of personalized content received from the substitute document server in response to the request; and
  providing the modified version of the document to a user set device that displays the modified version of the document to the user, wherein a first portion of the original content in the document that is replaced is selected based upon the identifier portion in the original content.

* * * * *

UNITED STATES PATENT AND TRADEMARK OFFICE
CERTIFICATE OF CORRECTION

| | | |
|---|---|---|
| PATENT NO. | : 7,814,143 B2 | Page 1 of 1 |
| APPLICATION NO. | : 11/301331 | |
| DATED | : December 13, 2005 | |
| INVENTOR(S) | : Stephen J. Brown et al. | |

It is certified that error appears in the above-identified patent and that said Letters Patent is hereby corrected as shown below:

Column 12, claim 1, line 53, delete "with".

Column 13, claim 5, line 6, replace "personalized" with "the personalized content".

Column 13, claim 11, line 30, delete "i0".

Column 13, claim 15, line 50, insert --the-- before --personalized--.

Column 13, claim 16, line 53, insert --the-- before --personalized--.

Column 14, claim 19, line 9, delete "5".

Column 14, claim 19, lines 16-17, delete "by parsing".

Column 14, claim 19, line 19, insert --the-- before --document--.

Column 14, claim 20, line 34, replace "profile and," with "profile, and".

Signed and Sealed this

Twenty-third Day of November, 2010

David J. Kappos
*Director of the United States Patent and Trademark Office*